(12) United States Patent
Lopez et al.

(10) Patent No.: US 6,200,567 B1
(45) Date of Patent: Mar. 13, 2001

(54) THERAPEUTIC AGENTS AS CYTOKINE ANTAGONISTS AND AGONISTS

(75) Inventors: Angel Lopez; Christopher Bagley; Joanna Woodcock, all of Adelaide (AU)

(73) Assignee: Medvet Science Pty Ltd (AU)

( * ) Notice: Subject to any disclaimer, the term of this patent is extended or adjusted under 35 U.S.C. 154(b) by 0 days.

(21) Appl. No.: 09/117,399

(22) PCT Filed: Jan. 29, 1997

(86) PCT No.: PCT/AU97/00049

§ 371 Date: Jul. 29, 1998

§ 102(e) Date: Jul. 29, 1998

(87) PCT Pub. No.: WO97/28190

PCT Pub. Date: Aug. 7, 1997

(30) Foreign Application Priority Data

Jan. 30, 1996 (AU) .................................................. PN7800

(51) Int. Cl.[7] ........................ A61K 39/395; G01N 33/53; C07K 16/28
(52) U.S. Cl. ..................................... 424/143.1; 424/130.1; 424/139.1; 514/2; 514/23; 435/7.1; 530/389.1
(58) Field of Search .............................. 424/143.1, 130.1, 424/139.1; 514/2, 23; 530/389.1; 435/7.1

(56) References Cited

PUBLICATIONS

Biro, et al., "The effect of WSEWS pentapeptide and WSEWS–specific monoclonal antibodies on consitutive and IL–6 induced acute–phase protein production by a human hepatoma cell line, HEPG–2", *Immunology Letters*, 46 (1995) 183–187.

Bagley et al., "Interaction of GM–CSF and IL–3 with the common β–chain of their receptors", *Journal of Leukocyte Biology*, 57 (1995) 739–746.

Devos et al., "Interleukin–5 and its receptor: a drug target for eosinophilia associated with chronic allergic disease", *Journal of Leukocyte Biology*, 57 (1995) 813–819.

Bazan, "Structural design and molecular evolution of a cytokine receptor superfamily", *Proc. Natl. Acad. Sci.*USA, 87 (1990) 6934–6938.

Watanabe et al., Monoclonal Antibody Against theCommon βSubunit ($\beta_c$) of the Human Interleukin–3 (IL–3), IL–5 and Granulocye–Macrophage Colony–Stimulating Factor Receptors Shows Upregulation of $\beta_c$ by IL–1 and Tumor Necrosis Factor–α, *Blood*, 80(9) (1992) 2215–2220.

*Primary Examiner*—Christine Saoud
*Assistant Examiner*—Fozia Hamud
(74) *Attorney, Agent, or Firm*—Henry D. Coleman; R. Neil Sudol (57) ABSTRACT

A therapeutic agent capable of of binding to the F'-G' loop of domain 4 of the common $_c$ Chain of the receptor for GM-CSF, IL-3, and IL-5. The amino acid $Tyr^{421}$ which is located in the F'-G' loop is critical in the high affinity binding and stimulation of function of GM-CSF, IL-3 and IL-5 to the common $_c$ chain of the receptors. Other receptors for cytokines also show hydrophobic amino acids in analogous positions and it is probable that they too play a pivotal role in binding of respective cytokines to them and in modulating function. Agents capable of binding to the F'-G' loops are suggested and should be of therapeutic value.

5 Claims, 7 Drawing Sheets

```
                      SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 9 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 1:

Thr  Ser  Arg  Thr  Gly  Tyr  Asn  Gly  Ile
 1                    5

(2) INFORMATION FOR SEQ ID NO:2:

(i) SEQUENCE CHARACTERISTICS:
        (A) LENGTH: 8 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 2:

Cys  Ser  Thr  Glu  Thr  Phe  Trp  Lys
 1                    5

(2) INFORMATION FOR SEQ ID NO:3:

(i) SEQUENCE CHARACTERISTICS:
        (A) LENGTH: 9 amino acid residues
        (B) TYPE: amino acid
        (D) TOPOLOGY: linear
```

```
    (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 3:

Cys Met Lys Glu Asp Gly Lys Gly Tyr
 1               5

(2) INFORMATION FOR SEQ ID NO:4:

(i) SEQUENCE CHARACTERISTICS:
        (A) LENGTH: 8 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 4:

Pro Leu Gln Gly Glu Phe Thr Thr
 1               5

(2) INFORMATION FOR SEQ ID NO:5:

(i) SEQUENCE CHARACTERISTICS:
        (A) LENGTH: 13 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 5:

Val Lys Thr Asn Lys Leu Cys Phe Asp Asp Asn Lys Leu
 1               5                  10              13

(2) INFORMATION FOR SEQ ID NO:6:

(i) SEQUENCE CHARACTERISTICS:
        (A) LENGTH: 6 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 6:

Glu Arg Val Tyr Glu Phe
 1               5

(2) INFORMATION FOR SEQ ID NO:7:

(i) SEQUENCE CHARACTERISTICS:
        (A) LENGTH: 8 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily
```

(xi) SEQUENCE DESCRIPTION: SEQ ID NO: 7:

Ala  Ala  Asp  Val  Arg  Ile  Leu  Asn
1                 5

(2) INFORMATION FOR SEQ ID NO:8:

(i) SEQUENCE CHARACTERISTICS:
        (A) LENGTH: 12 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 8:

Ala  Ala  Val  Ser  Ser  Met  Cys  Arg  Glu  Ala  Gly  Leu
1                 5                             10

(2) INFORMATION FOR SEQ ID NO:9:

(i) SEQUENCE CHARACTERISTICS:
        (A) LENGTH: 9 amino acid residues
        (B) TYPE: amino acid
        (D) TOPOLOGY: linear (ii) MOLECULE TYPE: peptide
        (A) DESCRIPTION: Amino acids that are part of the
            F'-G' loops of members of the cytokine receptor
            superfamily (xi) SEQUENCE DESCRIPTION: SEQ ID NO: 9:

Met  Ala  Glu  Pro  Ser  Phe  Gly  Gly  Phe
1                 5

(2) INFORMATION FOR SEQ ID NO:10:

(i) SEQUENCE CHARACTERISTICS:
        (A) LENGTH: 9 amino acid residues
        (B) TYPE: amino acid
        (D) TOPOLOGY: linear (ii) MOLECULE TYPE: peptide
            A) DESCRIPTION: Amino acids that are part of the
            F'-G' loops of members of the cytokine receptor
            superfamily (xi) SEQUENCE DESCRIPTION: SEQ ID NO: 10:

Leu  Asn  Gly  Pro  Thr  Tyr  Gln  Gly  Pro
1                 5

(2) INFORMATION FOR SEQ ID NO:11:

(i) SEQUENCE CHARACTERISTICS:
        (A) LENGTH: 9 amino acid residues
        (B) TYPE: amino acid
        (D) TOPOLOGY: linear (ii) MOLECULE TYPE: peptide
            A) DESCRIPTION: Amino acids that are part of the
            F'-G' loops of members of the cytokine receptor
            superfamily (xi) SEQUENCE DESCRIPTION: SEQ ID NO: 11:

Cys  Lys  Arg  Leu  Asp  Gly  Leu  Gly  Tyr
1                 5

```
(2) INFORMATION FOR SEQ ID NO:12:

(i) SEQUENCE CHARACTERISTICS:
         (A) LENGTH: 10 amino acid residues
         (B) TYPE: amino acid
         (D) TOPOLOGY: linear (ii) MOLECULE TYPE: peptide
         (A) DESCRIPTION: Amino acids that are part of the
              F'-G' loops of members of the cytokine receptor
              superfamily (xi) SEQUENCE DESCRIPTION: SEQ ID NO: 12:

Phe  Asn  Pro  Leu  Cys  Gly  Ser  Ala  Gln  His
1                   5                        10
```

THERAPEUTIC AGENTS AS CYTOKINE ANTAGONISTS AND AGONISTS

RELATED APPLICATIONS

This application is a 371 of WO97/28190, filed Jan. 29, 1997.

FIELD AND BACKGROUND OF THE INVENTION

This invention relates to antagonists and agonists of cytokines, the therapeutic use of such antagonists and agonists, and method of isolation of such antagonists and agonists.

BACKGROUND OF THE INVENTION

Human granulocyte-macrophage colony-stimulating factor (GM-CSF), interleukins IL-3 and IL-5 are cytokines involved in hemopoietic cell survival, production and function (reviewed in Lopez et al, 1992). Because of these properties, IL-3 and GM-CSF are currently being used clinically for bone marrow reconstitution following chemotherapy and radiotherapy (Groopman et al, 1987). However, it is also becoming apparent that excessive or aberrant production of GM-CSF, IL-3 and IL-5 can lead to disease states. For example, elevated amounts of GM-CSF have been found in the lungs of allergic individuals (Kato et al, 1992) and in the joints of patients with rheumatoid arthritis (Williamson et al, 1988). Elevated mRNA for IL-3,GM-CSF and IL-5 have been found in the skin of allergic individuals (Kay et al, 1991). GM-CSF can stimulate the proliferation of leukaemic cells (Young et al, 1986), and IL-3 has been shown to be produced by follicular B cell lymphomas in an autocrine fashion resulting in the proliferation of these cells in an IL-3-dependent manner (Clayberger et al, 1991).

It is clear from these clinical situations that antagonising GM-CSF, IL-3 and IL-5 can be of therapeutic value, and depending on the condition in question, antagonising one of these cytokines may be sufficient.

A number of suggestions for antagonists have already been made, for example in specification PCT/AU89/00177 and in specification PCT/AU94/00432 variants of GM-CSF are identified as antagonists to GM-CSF action however there is no indication that these antagonists are effective for more than only GM-CSF action.

However, in other situations the simultaneous antagonism of all three GM-CSF, IL-3 and IL-5 may be desirable or indeed necessary. For example, eosinophils which are believed to be the major cell type involved in allergy can be maintained in numbers and be stimulated by either IL-3, GM-CSF or IL-5 (Lopez et al, 1989). Antagonism of all three cytokines may thus be necessary to inhibit the actions of eosinophils and basophils. Similarly, basophils which are also believed to play an effector role in allergy can be stimulated by either IL-3,GM-CSF or IL-5 (Lopez et al., 1990) Antagonism of GM-CSF, IL-3 and IL-3 may be accomplished by the concomitant administration of specific antagonists for each different cytokine. Though feasible, this approach has the disadvantage of having to administer up to three different proteins which is not only inconvenient but which also increases the risk of immunogenicity and other side-effects.

SUMMARY OF THE INVENTION

One condition which is prevalent that may be exacerbated by elevated levels of these three cytokines is asthma. The roles of GM-CSF, IL-3 and IL-5 in asthma and allergy have been and continue to be extensively studied. Several studies have shown, by in site hybridisation, increased levels of IL-5 mRNA in lung mononuclear cells (Fukuda et al., 1994; Robinson et al., 1992; Marini et al., 1992; Hamid et al., 1991) and in eosinophils (Broide et al., 1992) in asthmatic patients. Immunochemistry has also revealed increased amount of IL-5 protein in these tissues (Ackerman et al., 1994). In allergen-induced late-phase cutaneous reactions in atopic subjects increased mRNA for IL-5, IL-3 and GM-CSF have been noted (Kay etal., 1991).

BRIEF DESCRIPTION OF THE DRAWINGS

Bronchoalveolar lavage (BAL) fluids from symptomatic asthma patients had greater IL-5 levels than patients with asymptomatic asthma (Sur et al., 1995). Furthermore when symptomatic asthma patients were challenged with antigen in one lung segment, significant levels of IL-5 were noted (980 pg/ml) compared with sham challenged segment of the same patient (2.8 pg/ml) (Sur et al, 1995). In another study with similar design IL-5 levels increased from undetectable to 2800 pg/ml in both allergic and non-allergic asthmatics (Zangrilli et al., 1995). A causal relationship between levels of IL-5 and asthma is suggested from studies in which treatment of moderately severe asthmatic patients with corticosteroids for two weeks resulted in a reduction of the number of cells expressing IL-5 mRNA (Bentley et al., 1996). This reduction was correlated with clinical improvement and also with loss of $CD3^+$ T cells and activated ($EG2^+$) eosinophils.

DESCRIPTION OF THE PREFERRED EMBODIMENTS OF THE INVENTION

GM-CSF has also been detected in the lungs of asthmatics. Indeed in one study of sputum cytokines, GM-CSF appeared to have the dominant effect on eosinophil survival (Adachi et al., 1995).

IL-5 also activates eosinophils to express the EG2 epitope. In several studies increased IL-5 levels were associated with $EG2^+$ eosinophils in the lung (Fukuda et al., 1994; Bentley et al., 1996). Furthermore there is evidence of a tissue-specific activation of eosinophils. In one experiment, activation of eosinophils in the lung was compared to those in the blood of the same patient. Activation was assessed by cell surface expression of CR-3, p150/95, CD67, CD63 and loss of L-selecting. In patients challenged with endobronchial antigen both peripheral and lung eosinophila were seen at 24h, however only lung eosinophils had increased levels of GM-CSF mRNA suggesting a local activation of these cells. In addition, there was evidence of activation in lung-derived eosinophils but not those from blood. This result is compatible with a specific effect of IL-5 on lung eosinophils and their involvement in asthma.

Animal models also suggest a role for IL-5 in asthma. The most significant data exists with an antibody (TRFK-5) against IL-5 in monkey models of asthma (Mauser et al., 1995). Ascaris-sensitive cynomolgus monkeys were challenged with aerosolised *Ascaris sum* extracts. 0.3mg/kg TRFK abolished increased airway reactivity and diminished eosinophil numbers in BAL fluids. Interestingly this inhibition persisted for 3 months (Mauser et al., 1995). Guinea pig studies supported this conclusion (Mauser et al., 1993). Furthermore mice in which the IL-5 gene was genetically ablated not only had no detectable IL-5 and significant reduction in eosinophil numbers but also developed significantly less severe asthma (as manifest by airways hyperreactivity and lung damage) than IL-5 gene positive littermates (Foster et al., 1996). A clear example of restoration of airway responsiveness to methacholine was seen after IL-5 deficient mice were given IL-5 expressing-, but not control-, vaccinia virus infections (Foster et al., 1996).

A likely role for GM-CSF in asthma has also been suggested by over expression of GM-CSF in rat lung leading to eosinophilia, macrophage granuloma and fibrotic reaction, a triad also seen in asthma (Xing et al 1996)

Human interleukin (IL)-3, granulocyte-macrophage colony-stimulating factor (GM-CSF) and IL-5 exert their biological effect by binding to specific surface receptors on the surface of cells (Bagley et al, 1995; Elliott et al, 1989; Park et al, 1989; Lopez et al, 1991). The receptors are heterodimers comprising an a chain which is specific for each ligand, and a β chain ($\beta_c$) which is shared between the three receptors (Lopez et al, 1992; Kitamura et al, 1991). Whilst each ligand binds to the respective α chain, $\beta_c$ provides high affinity binding and allows signalling (Miyajima et al, 1992 and U.S. Pat. No. 5,112,961 by Hayashida et al)). The inventors in U.S. Pat. No. 5,112,961 suggest that the high affinity receptor is a valuable tool for screening candidate GM-CSF agonists and antagonists.

Because all three of these cytokines act through a common receptor subunit ($\beta_c$) we previously hypothesised (Bagley et al, 1995, which reference is incorporated herein), it may be possible to simultaneously inhibit the action of GM-CSF, IL-3 and IL-5 with a single compound. There has, however, to date been no means whereby to approach the problem of finding an effector that acts co-ordinately on all three cytokines. It is not clear, for example, what region of the common receptor subunit ($\beta_c$) is being bound by these cytokines, and whether the same region is bound for all three cytokines or whether three different regions are involved.

Analysis of the $\beta_c$ has shown that it contains four extracellular domains (Goodall et al, 1993) with domain 1 representing the most N-terminal domain and domain 4 representing the most membrane proximal domain. Each domain consists of seven β strands linked together by intervening loops. The loop of interest, the F'-G' loop, is located in domain 4 of $\beta_c$. The residues of interest are numbered from the N-terminus at primary translation terminus with the initiation methionine being $Met^1$.

The molecular basis for the affinity conversion of $\beta_c$ to each ligand is not fully understood as the ligand-receptor complex has not yet been crystallised. However, by analogy to the interaction of growth hormone (GH) with its homodimeuic receptor (DeVos et al, 1992) there is likely to be direct interaction between ligand and receptor α and β chains. In the GH:GH receptor system the contact points between GH and GHbp2 have been determined from X-ray crystallography of the GH:GHbp1 and 2 complex (DeVos et al, 1992). By analogy with this system we (Woodcock et al, 1994) and others (Lock et al, 1994) have previously shown that the B'-C' loop of $\beta_c$ plays some role in high affinity binding of GM-CSF, IL-3 and IL-5. Specifically it has been shown that three residues, $Tyr^{365}$, $His^{367}$ and $Ile^{368}$ are important for GM-CSF and IL-5 high affinity binding but are only marginally involved in IL-3 high affinity binding (Woodcock et al, 1994). These results imply that targeting these three amino acids with appropriate compounds may impair GM-CSF and IL-5 but not IL-3-mediated activity.

SUMMARY OF THE INVENTION

Using molecular modelling techniques we have recently postulated that the F'–G' loop may be involved in ligand binding (Bagley et al, 1995). The invention arises out of an investigation on this predicted F'–G' loop of $\beta_c$ and from the finding that this loop is essential for the high affinity binding and signalling of all three cytokines GM-CSF, IL3 and IL-5.

A further aspect of this invention arises as a result of the surprising identification of a single amino acid in the receptor oc chain for GM-CSF, IL-3 and IL-5 which is necessary for the high affinity binding of all of these three ligands to their surface receptors and for signalling and the fact that all three of these cytokines require the F'-G' loop for high affinity conversion. It is believed that compounds that bind to $Tyr^{421}$ or inhibit the binding of ligand to $Tyr^{421}$ will behave as generic antagonists of IL-3, GM-CSF and IL-5.It is thought that compounds that bind to the F'-G' loop will sterically inhibit this binding.

Additionally this finding is likely to have implications for other members of the cytokine receptor superfamily some of which are shared subunits in a given subfamily (that is they bind several cytokines), and some which are ligand specific and bind to only one cytokine. The receptor α-chains for GM-CSF, IL-3 and IL-5 and $\beta_c$ belong to the rapidly expanding cytokine receptor superfamily. Within this superfamily several sub-families are now emerging that are characterized by the sharing of a communal receptor subunit by multiple ligands: gp1130 acts as an affinity converter and signal transducer for IL-6 (Hibi et al., 1990; Taga et al., 1992), IL-11 (Hilton et al., 1994), oncostatin M (Liu et al., 1992), ciliary neurotrophic factor, leukaemia inhibitory factor (LIF) (Ip et a., 1992) and cardiotrophin-1 (Pennica et al., 1995); the LIF receptor (LIFR) also binds ciliary neurotrophic factor (Davis et al., 1993), cardiotrophin-1 (Pennica et al., 1995) and oncostatin M in addition to LIF (Gearing et al., 1994); IL-2R β supports affinity conversion and signalling of IL-2 and IL-15 (Giri et al., 1994); IL-2R γ chain affinity converts IL-2 (Takeshita et al., 1992), IL-4 (Russell et al., 1993), IL-7 (Noguchi et al., 1993), IL-9 (Kimura et al., 1995)and IL-15 (Giri et al., 1994); evidence also suggests that IL-4 and IL-13 share a receptor component (Zurawski et al., 1993) and this subunit has recently been cloned (Hilton et al., 1996). It is not known which residues in gp130, LIFR and IL-2R β and γ chains are important for ligand binding or indeed whether different ligands share or have unique sets of binding determinants on these communal receptor subunits. Because these common subunits are vital for transducing signals by several ligands, the possibility arises that interfering with the ability of these common subunits to bind ligand or to form homodimers may affect the action of more than one ligand.

An alignment of the predicted F'-G' loop of $\beta_c$ with that of several common as well as ligand-specific receptor subunits revealed the presence of tyrosine and other similarly hydrophobic residues in this region (Table 3). Although the exact length of this putative loop varies between 7–14 amino acids amongst the different receptors, it is constrained by two strongly conserved sequences; the VRVR consensus at the N terminus and the WSXWS consensus at the C terminus. It is suggested that although the nature of the ligand-receptor interaction will be specific to the system involved, the hydrophobic aromatic residues in the receptor represent strong candidates for ligand interaction. Thus members of the cytokine receptor family may use a structurally conserved receptor framework to display a series of loops that through predominantly hydrophobic interactions support the binding of specific ligands. Support for this notion also stems from mutational afnalysis of the IL-6R which showed that a mutant in which both $Glu^{297}$ and $Phe^{298}$ in the F'-G' loop were substituted exhibited loss of IL-6 binding (Yawata et al., 1993).

A recent analysis of the residues involved in binding growth hormone in GHR revealed that the greatest contribution to affinity came from hydrophobic interactions (Clackson and Wells, 1995). Systematic alanine substitution of the 33 residues in GHR known to be inaccessible to solvent upon growth hormone binding showed that substitution of only eleven of these residues had any significant effect on affinity and, of these, six were hydrophobic. Furthermore these hydrophobic residues are clustered on the surface of GHR in a region which forms the interface for interaction with growth hormone. In addition, in GHR the greatest reduction in affinity occurred on substituting two tryptophan residues (Clackson and Wells, 1995; Bass et al., 1991) implicating hydrophobic aromatic residues as being very important for ligand interaction. From our present study and our. previous work (Woodcock et al., 1994) we have now identified a total of three hydrophobic residues in predicted loops which play a role in ligand interaction in $\beta_c$, $Tyr^{365}$, $Ile^{368}$ and $Tyr^{421}$. Thus it appears that binding of $\beta_c$ to GM-CSF, IL-3 and IL-5 is also supported predominantly by hydrophobic interaction.

It is interesting to compare these findings with $\beta_c$ of GM-CSF, IL-3 and IL-5 receptors with the crystal structure and mutational analysis of the GH-GHR. In contrast to the heterodimeuic nature of the GM-CSF, IL-3 and IL-5 receptors, the GHR is a homodimer. The two identical subunits of GHR bind growth hormone sequentially and in a non-equivalent manner. In the crystal structure, the two growth hormone-binding proteins are correspondingly identified as GHbpI and GHbpII. The initial interaction of GHbpI utilises sites I contacts in growth hormone and is relatively strong with a dissociation constant of 600 pM (Cunningham et al., 1991). Subsequent interaction with GHbpII through site II contacts decreases the dissociation constant to 200 pM. Therefore, interaction of GHbpII with growth hormone bound to GHbpI confers a 3-fold increase in affinity on the receptor complex. Thus, functionally, human $\beta_c$ is analogous to GHbpII, binding only after initial association of ligand with receptor α-chain and conferring up to 1000-fold increase in affinity on the receptor complex (as in the case of IL-3). The results presented here, however, show three significant differences from the GH-GHR interaction. First, the F'-G' loop in GHbpI and not in GHbpII (analogous to $\beta_c$) is involved in ligand binding. Second, although residues in the F'-G' loop of GHbpI are effectively solvent excluded on binding of growth hormone, indicating close contact between ligand and receptor, there is seemingly very little productive interaction between the two proteins in this region. Alanine-scanning mutagenesis across residues of this loop in GHR had very little effect on growth hormone binding affinity relative to wild type receptor (Clackson and Wells, 1995; Bass et al., 1991). Hence the contact between the F'-G' loop of GHbpI and growth hormone contributes little to the binding affinity of the receptor. This is in contrast to our findings here, where we observe complete loss of affinity conversion for all ligands on substitution of $Tyr^{421}$, indicating a very strong interaction between this residue and ligand in the wild type molecule. Third and consistent with the lack of productive interaction between the F'-G' loop of GHR and GH, there are no hydrophobic residues in this loop. Thus despite GHR using contact sites of a clearly hydrophobic nature, these lie elsewhere in this receptor, indicating that the contribution made to affinity by the various contact sites is different in $\beta_c$ relative to GHR.

In a first broad aspect the invention could therefore be said to reside in a therapeutic agent capable of binding to the F'-G' loop of domain 4 of the common $\beta_c$ chain of the receptor for GM-CSF, IL-3 and IL-5, or to an analogous loop of another cytokine receptor the binding of which agent has an antagonist or agonist effect on the respective cytokine or one of the cytokines.

In a first form of the first aspect the cytokine receptor is a common signal transducing receptor, which may be one selected from the group comprising $\beta_c$, gp130, LIFR, IL-2Rβ IL-2Rγ, and IL-4R/IL-13R. In a more specific form of this aspect the receptor is $\beta_c$. In a preferred form of this aspect the agent has the antagonist or agonist effect on all respective cytokines that bind to the receptor.

In a second form of the first aspect of the invention the F'-G' loop includes a hydrophobic amino acid. The aromatic hydrophobic amino acid for the respective receptor may be as indicated in Table 3 and the invention may be restricted to the receptor listed therein, or may be to a tyrosine and the invention may be restricted to receptors with a tyrosine present in the F'-G' loop. The receptor may alternatively be restricted to those receptors that also interact with $\beta_c$.

In a third form of the first aspect of the invention the cytokine receptor is a signalling receptor, which in one more specific form is specific for a single cytokine, and may be selected from the group comprising EPOR, TPOR and OBR.

As indicated above in the more specific form of the first form of the first aspect of the invention the common signal transducing receptor is $\beta_c$. The amino acid specificity at position 421 is quite stringent and the therapeutic agent may need to be identified as requiring the presence of $Tyr^{421}$ for binding, or of sterically hindering the normal interaction that $Tyr^{421}$ has. The agent may be capable of alleviating the symptoms of asthma.

The therapeutic agent may take the form of any one of a number of classes of compounds and may be selected from a group comprising, antibodies, peptides, oligosaccharides, oligonucleotides, or other organic or inorganic compounds.

In a second aspect the invention could be said to reside in a method of isolating a therapeutic agent capable of binding to the F'-G' loop of domain 4 of the common $\beta_c$ chain of the receptor for GM-CSF, IL-3 and IL-5, or to an analogous loop of another cytokine receptor, said method including the steps of screening candidate molecules for their capacity to bind to the said loop. In one form of this second aspect of the invention the step of screening candidate molecules for their capacity to bind to said loop, comprises screening for the capacity to bind to a sequence selected from the group comprising SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12. It will also be understood that as an alternative only the loop to be screened may be selected from those derived from a common signal transducing receptor, or as a second alternative from those receptors having a hydrophobic amino acid residue, or as a third alternative from those receptors that are signal transducing receptors.

Alternative the invention could be said to reside in a method of isolating a therapeutic agent, by screening for the ability of compounds to bind to $Tyr^{421}$ of the common $\beta_c$ chain of the receptor for GM-CSF, IL-3 and IL-5, or the corresponding aromatic hydrophobic residue of gp130 or to an analogous aromatic hydrophobic residue of another common signal transducing receptor or of a specific receptor responsive to other cytokines.

The agent may be an antibody or fragment thereof and the method of isolating such an antibody will be understood to further including the steps of inoculating an animal with a peptide molecule having the F'-G' loop, fusing antibody producing cells with a myeloma cell line and screening for a cell line that produces an antibody reactive with said F'-G' loop, and harvesting antibodies from said cell line, testing for inhibition of high affinity binding and testing for inhibition or excitation of function. This may further include making small figments of antibodies produced by the said cell line capable of binding said the loop. The cell line may conveniently be a mouse cell line and the method may include the further step of humanising the said antibody fragments by replacing mouse sequences with human sequences in the non-binding regions.

In a third aspect the invention could be said to reside in a method of treating an human or an animal for a condition, said method including the step of administering a therapeutic agent as identified above in a pharmaceutically acceptable carrier and in a therapeutically effective dose.

It may be desired to treat the condition with one or more of the therapeutic agents identified or defined herein in combination, and perhaps in combination with other therapeutic agents.

The treatment may be aimed at being preventative by reducing the risk of contracting the condition, or the treatment may be used to alleviate or obviate the condition. The administration of the therapeutic agent can be any pharmaceutically acceptable form and in a suitable carrier.

It is thought that the construction of compounds that bind the F'-G' loop of $\beta_c$ will be therapeutically useful for intervention in conditions where IL-3, GM-CSF and IL-5 play a pathogenic role, mainly allergy, asthma, leukaemia, lymphoma and inflammation including arthritis.

Similarly for other cytokine receptors it is thought that antagonists or agonists will be therapeutically useful. Thus for common signal transducing receptors. Since gp1130 is functionally analogous to $\beta_c$ in the GM-CSF/IL-3/IL-5 receptor system, in that it is a common binding sub-unit and signal transducer for the IL-6, oncostatin M (OSM), ciliary neurotrophic factor (CNTF), leukaemia inhibitory factor (LIF) and IL-11, it is suggested that targeting/blocking of this tyrosine will lead to antagonism of the IL-6, LIF, OSM, CNTF and IL-11. Antagonism of this receptor system will be useful in inflammation, leukaemia and lymphoma. Antagonists of IL-2R$\beta$/$\gamma$ may be useful as immunosuppressants. Antagonists of LIFR may be useful for the prevention of implantation of embryos in uteri. Antagonist of IL-4/IL-13 will inhibit IgE production and may be useful in treating asthma and allergies.

For specific subunits. Antagonist of IL-3 may be useful in treating allergy and follicular B cell lymphoma. Antagonists of IL-4 may inhibit IgE production, and be useful for treatment of asthma and allergy. Antagonists of IL-6R may be useful as an anti-inflammatory and may be used to inhibit mycloma growth. Antagonists against IL-7 may be useful as an immunosuppressant. Antagonists of the leptin receptor (OBR) may be useful in the treatment of cachexia, weight loss in conditions such as AIDS, cancer, and parasitic diseases.

It can be seen that an antagonist effect has been found, however, it is to be understood that the invention may also encompass agonists. The residue identified clearly plays a pivotal role in the action of the system and whilst some molecules that interact with the F'-G' loop of $\beta_c$ or corresponding residues in other receptors (such as shown in table 3) can be expected to have an antagonist effect it is equally possible that they have an agonist effect particularly in receptors that can be activated by homodimerization.

Firstly the common signal transducing receptors. Agonists agents that bind to $\beta_c$ may be used to stimulate hemopoiesis, and to boost immune response against microorganisms. Agonists agents that bind to LIFR may be useful in the suppression of embryonic stem cell differentiation. Agonists agents that bind to IL-2R$\beta$ may be used in immunostimulation. Agonists agents that bind to IL-4R/IL-13 may have anti-tumour activity.

Turning now to specific subunits. Agonists agents that bind IL-3R may be use in the in vivo and ex vivo expansion of early hemopoietic cells. Agonists agents that bind to IL-4R may have useful anti-tumour activity. Agonists agents that bind to IL-7R may have useful anti-tumour immunity. Agonists agents that bind IL-11 may prove a useful adjunct to cancer therapy. Agonists agents that bind to EPOR may be used to correct anemia of chronic renal failure, of chronic inflammatory diseases and of malignant diseases. Agonists agents that bind to TPOR, may be useful for correcting thrombocytopenia (such as may be associated with chronic inflammatory diseases, malignancies, chemo- and radiotherapy).

Examples of useful agonists are those for erythropoiedin and thrombopoietin to elevate erythrocyte and platelet numbers in blood following blood cell loss, chemotherapy, radiotherapy, immunosuppression or bone marrow transplantation. Agonists of OBR may be used to induce weight loss, and in particular for obesity which is considered to be a contributing factor of hypertension, coronary heart disease and non insulin-dependent diabetes mellitus. The molecules whether agonist or antagonist can be isolated on the basis of their ability to interact with the identified residue.

By way of a shorthand notation the following three and one letter abbreviations for amino acid residues are used in the specification as defined in Table 1.

Where a specific amino acid residue is referred to by its position in the polypeptide of an protein, the amino acid abbreviation is used with the residue number given in superscript (i.e. Xaa$^n$)

TABLE 1

| Amino Acid | Three-letter Abbreviation | One letter Abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE DRAWINGS

FIG. 2 Are graphic representations showing that alanine substitution of residues 418–422 in $\beta_c$ abolishes high affinity GM-CSF and IL-3 binding. Scatchard transformation of saturation binding experiments using $^{125}$I-GM-CSF (left panel) and $^{125}$I-IL-3 (right panel) were carried out on COS cells expressing both GM-CSFR and IL-3R α-chains together with wild type (o) or mutant $^{418}$AAAAA$^{422}$ (●)$\beta_c$. The radio-iodinated ligand concentration range for both GM-CSF and IL-3 was 10 pM-10 nM and non-specific binding was determined in the presence of 1 μM unlabelled ligand. The broken line indicates the high and low affinity binding components using wild type $\beta_c$, and the solid line represents the line of best fit for the $^{418}$AAAAA$^{422}$ mutant $\beta_c$ as determined using the LIGAND program. A representative experiment is shown and the $K_d$ values derived from these and several other experiments are shown in Table 2.

DETAILED DESCRIPTION OF THE EXAMPLES

Example 1

Demonstrating the Efficacy of Tyr$^{421}$ in $\beta_c$ Subunit Binding

Rationale for Mutagenesis of Putative Loops in the Humian β Chain.

Figure 1A:
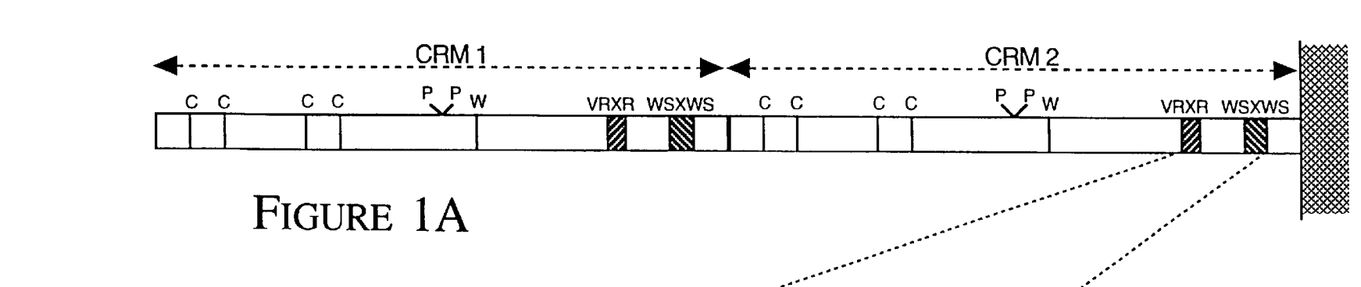
FIG. 1A Is a schematic representation of the extracellular domain of human $\beta_c$ showing two cytokine receptor modules (CRM1 & 2) (Goodall et al., 1993) and conserved features of the cytokine receptor superfamily (Bazan 1990).
Figure 1B:
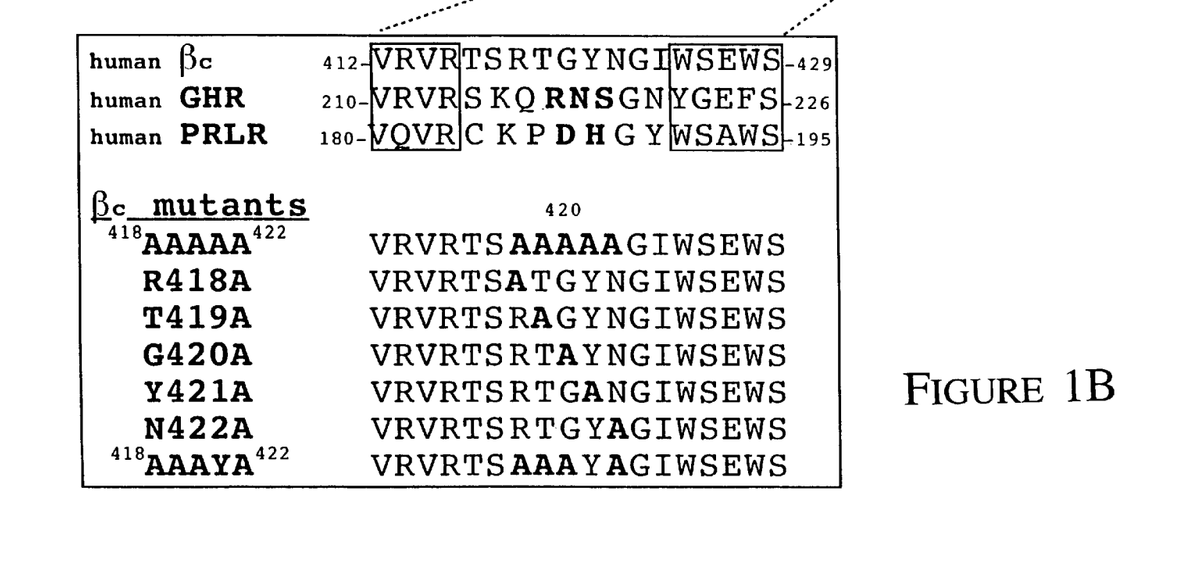
FIG. 1B Represents the amino acid sequences corresponding to the putative F'-G' loop in the membrane proximal CRM2 of $\beta_c$ (Hayashida et al., 1990) aligned with the F'-G' loops of growth hormone receptor (GHR) (Leung et al., 1987) and prolactin receptor (PRLR) (Boutin et al., 1988). Conserved structural motifs are boxed and previously identified residues that are involved in ligand (GH) contact (De Vos et al., 1992, and Somers et al., 1994) are shown in bold. Mutant forms of $\beta_c$ which were made to identify ligand binding determinants are shown with mutated residues in bold.

The region of $\beta_c$ we have targeted for mutagenesis is flanked by regions that show conservation throughout the cytokine receptor superfamily: the VRXR consensus described previously (Patthy 1990) where X most commonly represents an aliphatic residue, and the WSXWS motif (Cosman et al., 1990; Bazan 1990) (FIG. 1). The WSXWS motif has long been recognised as a characteristic feature of this receptor family and several studies have been directed towards understanding its role in receptor function (Miyazaki et al., 1991; Yoshimura et al., 1992; Quelle et al., 1992; Rozakis-Adcock and Kelly 1992; Baumgartner et al., 1994). The GH-GHR crystal structure (De Vos et al., 1992) and more recently the crystal structure of GH bound to prolactin receptor (Somers et al., 1994) gives us some insight into the structure of the VRXR-WSXWS region in cytokine receptors in general. The two β strands concerned interact exquisitely to form a stack of aromatic side-chains interleaved by the hydrophobic portions of the basic side-chains and as a consequence the amino acids separating these two motifs form a loop. Residues in this loop are solvent inaccessible in the ligand-bound complex in both resolved receptors (De Vos et al., 1992; Somers et al., 1994). We have therefore concentrated our attention here on the analogous F'-G' loop region in the membrane proximal cytokine receptor module (CRM) of $\beta_c$ to determine its role in GM-CSF, IL-3 and IL-5 binding.

Identifying a Region Involved in GM-CSF, IL-3 and IL-5 High Affinity Binding.

Figure 2:
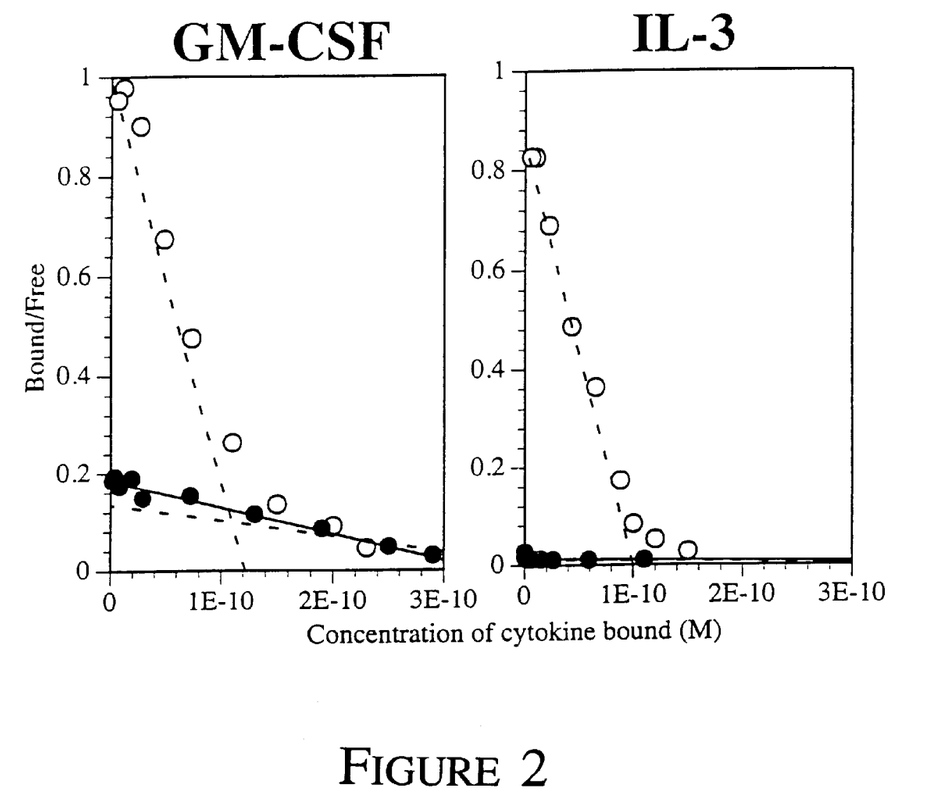

To investigate the possible involvement of the putative F'-G' loop of $\beta_c$ in high affinity receptor complex formation, the region was disrupted by substitution of alanines across residues 418–422 (FIG. 1). The ability of this n-alanine substituted mutant $\beta_c$ ($^{418}$AAAAA$^{422}$) to support high affinity ligand binding was studied by co-expressing it with both GM-CSFR and IL-3R α-chains on COS cells and performing radioligand saturation binding studies. Routinely COS cells were electroporated with both α-chain cDNAs together with mutant $\beta_c$ cDNA so that the same transfectant could be analysed for both GM-CSF and IL-3 binding. In the absence of transfected $\beta_c$, GM-CSFR and IL-3R α-chain transfected COS cells bound GM-CSF and IL-3 with low affinity only (Table 2). Co-expression of wild type $\beta_c$ conferred high affinity binding on GM-CSF and IL-3 but as the α-chains were expressed in excess of $\beta_c$, low affinity binding was still in evidence as represented by the curvilineauity of the corresponding Scatchard plots (FIG. 2, Table 2). COS cells transfected with mutant penta-alanine $\beta_c$ ($^{418}$AAAAA$^{422}$) GM-CSFR and IL-3R α-chain exhibited cell-surface expression of all receptor chains comparable to wild type transfectants (Table 2) but exhibited no high affinity binding of GM-CSF or IL-3 (FIG. 2, Table 2). This indicates that substitution of the region 418–422 in $\beta_c$ has interfered with the ability of $\beta_c$ to support high affinity GM-CSF and IL-3 binding and suggests that residues in this region may be involved in ligand interaction.

Tyr$^{421}$ is Necessary and Sufficient for GM-CSF, IL-3 and IL-5 High Affinity Binding.

Figure 3:
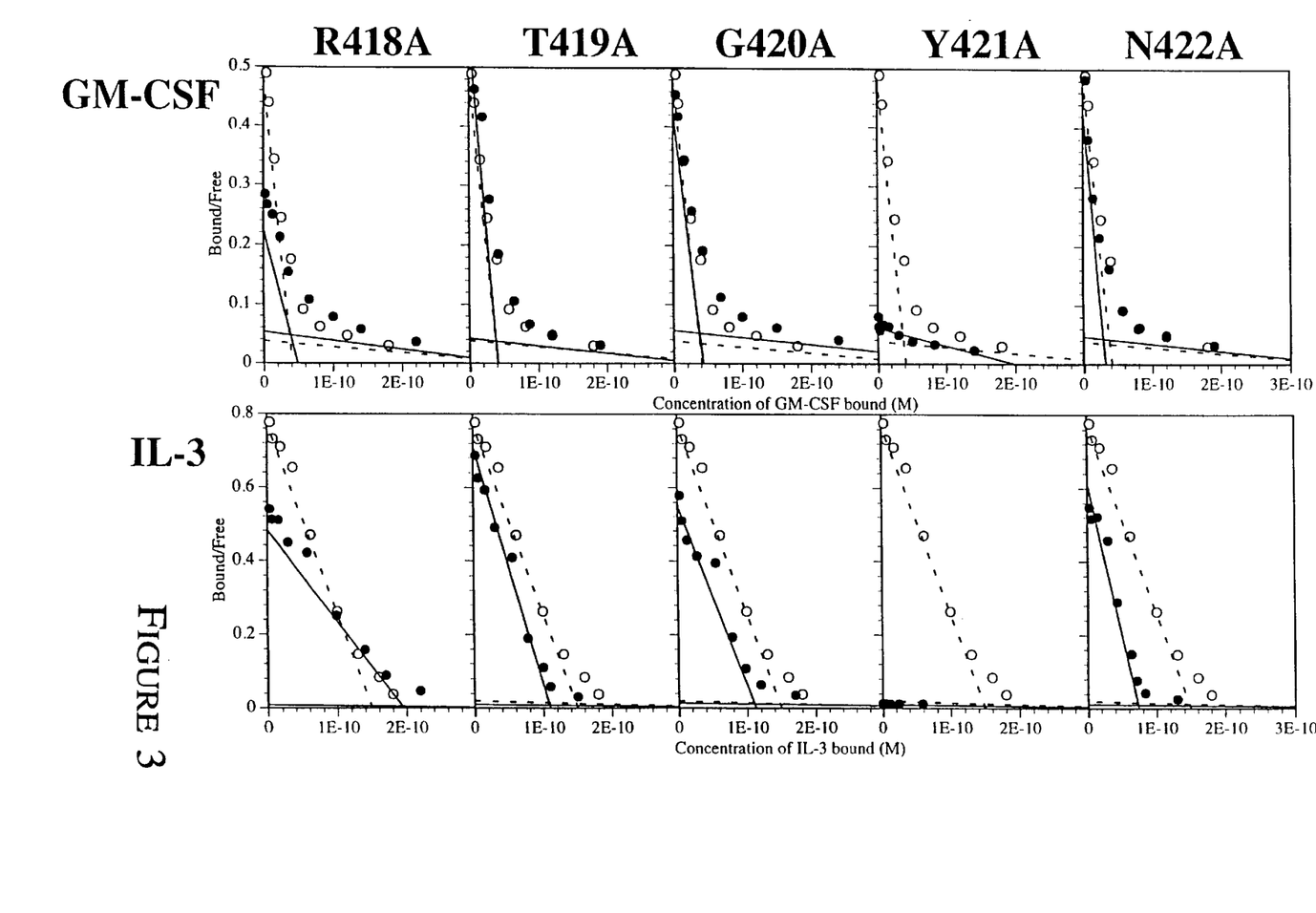
FIG. 3 Shows the effect of individual alanine substitution of residues Arg$^{418}$, Thr$^{419}$, Gly$^{420}$, Tyr$^{421}$ and Asp$^{422}$ of human $\beta_c$ on high affinity GM-CSF and IL-3 binding. Scatchard transformation of saturation binding studies with $^{125}$I-GM-CSF (top panel) and $^{125}$I-IL-3 (bottom panel) were carried out as described in FIG. 2. The broken line indicates the high and low affinity binding components using wild type $\beta_c$ (o), and the solid line represents the line of best fit for each mutant $\beta_c$ (●) as determined using the LIGAND program. A representative experiment is shown and the $K_d$ values derived from these and similar studies are shown in Table 2.

In order to examine the individual contribution of residues 418–422 of $\beta_c$ to high affinity GM-CSF, IL-3 and IL-5 binding, each residue in this region was substituted separately with alanine (FIG. 1). As above, the ability of individual mutants to mediate high affinity ligand binding was determined by carrying out radioligand saturation binding studies on COS cells expressing mutant $\beta_c$ together with GM-CSFR and IL-3R α-chains. Results showed that all alanine substitution mutants were cell surface expressed similarly to wild type $\beta_c$ (Table 2) and alanine substitution of residues Thr$^{419}$, Glu$^{420}$ and Asn$^{422}$ had no affect on high affinity ligand binding (FIG. 3, Table 2). Alanine substitution of Arg$^{418}$ reduced both GM-CSF and IL-3 high affinity binding by 2–3 fold which is a relatively small effect (Table 2). Interestingly, however, alanine substitution of Tyr$^{421}$ generated a $\beta_c$ mutant that was unable to support high affinity binding of either GM-CSF or IL-3 (FIG. 2, Table 2). The effect of this mutation on high affinity IL-5 binding was also determined by transfecting COS cells with mutant Y421A $\beta_c$ together with IL5R α-chain. The saturation binding data obtained with radio-iodinated IL-5 exhibited a single class of receptor on Scatchard analysis. Although $\beta_c$ has a small effect on affinity conversion of IL-5 binding relative to IL-3 and GM-CSF, studies with the mutant Y421 A $\beta_c$ showed a loss of affinity commensurate with the loss of high affinity IL-5 binding (Table 2). This shows that Tyr$^{421}$ has a similar role in supporting high affinity binding of GM-CSF, IL-3 and IL-5.

Figure 4:
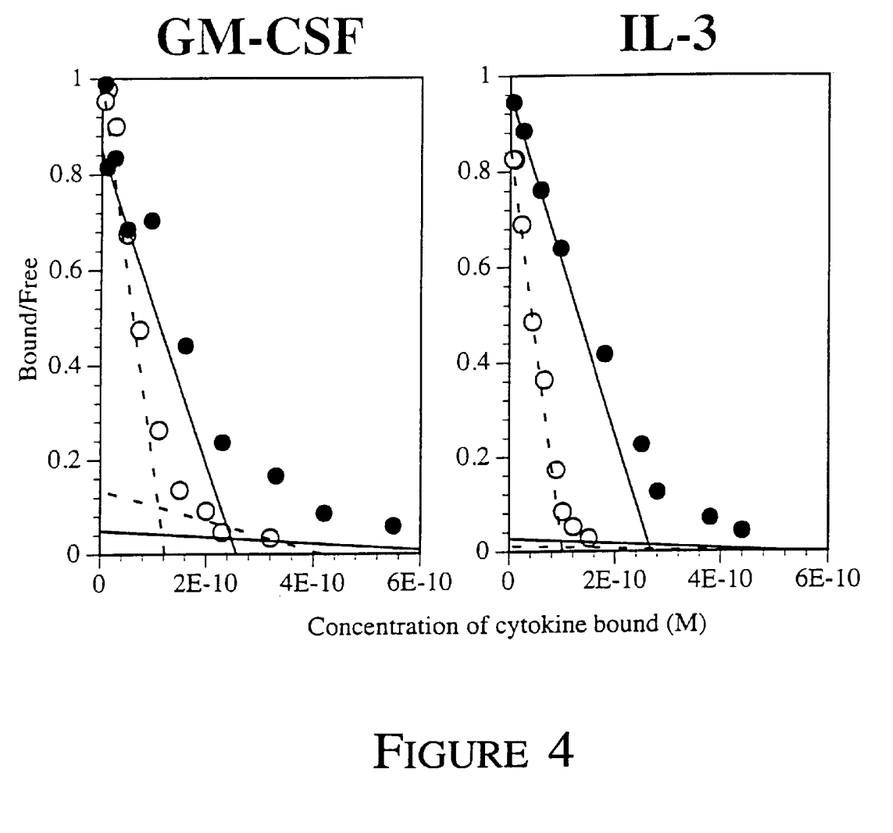
FIG. 4 Shows the effect of re-introducing Tyr$^{421}$ into a poly-alanine substituted $\beta_c$ ($^{418}$AAAYA$^{422}$) on high affinity GM-CSF and IL-3 binding. Scatchard transformation of saturation binding studies with $^{125}$I-GM-CSF (left panel) and $^{125}$I-IL-3 (right panel) were carried out as described in FIG. 2. The broken line indicates the high and low affinity binding components using wild type $\beta_c$ (o), and the solid line represents the line of best fit for the $^{418}$AAAYA$^{422}$ mutant $\beta_c$ (●) as determined using the LIGAND program. A representative experiment is shown and the $K_d$ values derived from these and similar studies are shown in Table 2.

The identification of a single residue in a predicted loop of the membrane proximal CRM of $\beta_c$ that is critical for high affinity GM-CSF, IL-3 and IL-5 binding raised the possibility that this residue alone in the context of a loop might be sufficient to support high affinity binding. To test this notion we re-introduced a tyrosine residue back into a poly-alanine substituted $\beta_c$ mutant ($^{418}$AAAYA$^{422}$) (FIG. 1). Surprisingly, this mutant was able to support high affinity GM-CSF and IL-3 binding (FIG. 4) albeit with a three fold reduced affinity relative to wild type GM-CSF and IL-3 high affinity binding (Table 2). This mutant also restored high affinity binding to IL-5 (Table 2). These findings indicate that the residues adjacent to Tyr$^{421}$ play no direct role in ligand interaction and implicate Tyr$^{421}$ as a key residue in GM-CSF, IL-3 and IL-5 high affinity binding.

Substinition of Tyr$^{421}$ Disrupts Functionial Receptor Activation.

Figure 5A:
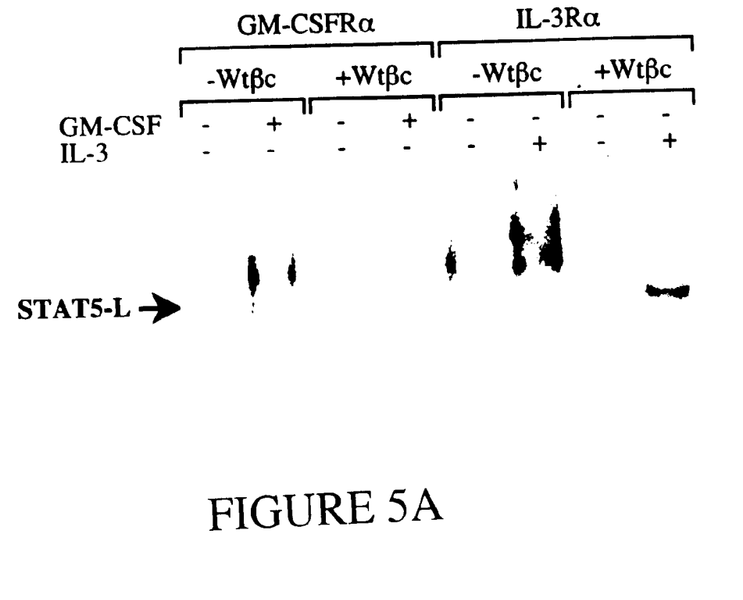
FIG. 5A Is a representation of an autoradiogram showing that STAT5-like (STAT5-L) activity is induced by GM-CSF and IL-3 only in Jurkat cells expressing appropriate α-chains together with wild type (Wt) $\beta_c$. Nuclear extracts were prepared from transfected Jurkat cells stimulated for 1 hr with or without 300 nM cytokine and analysed by electrophoretic mobility shift assay using a STAT5 specific probe.
Figure 5B:
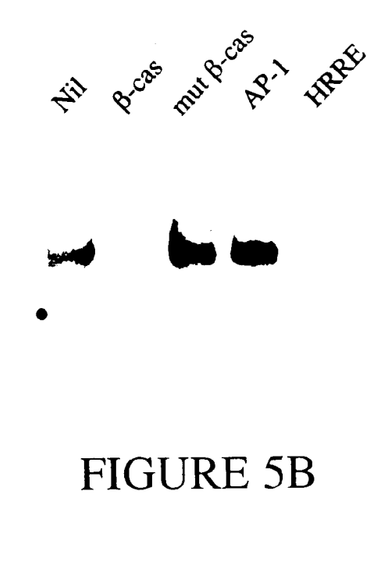
FIG. 5B Is a representation of an autoradiogram similar to that of FIG. 5A showing that the DNA binding protein induced by cytokine in receptor transfected Jurkat cells behaves like STAT5. Nuclear extract prepared from GM-CSF-stimulated transfected Jurkat cells was subjected to electrophoretic mobility shift assay in the presence of 50-fold molar excess of competing non-radioactive oligonucleotides. The oligonucleotides used for competition were: the β-casein promoter element (β-cas), a mutant of the β-casein promoter element (mut β-cas), an AP-1 consensus binding site (AP-1) and the haemopoeitin receptor response element (HRRE).

In order to determine the functional significance of substituting Tyr$^{421}$ of $\beta_c$ for alanine we measured the induction of signal transducers and activators of transcription (STAT). Productive interaction of GM-CSF, IL-3 and IL-5 with their high affinity receptors leads to signal transduction mediated by $\beta_c$ (Kitamura et al., 1991b; Kitamura et al., 1992; Takaki et al., 1993). It is now well documented that signalling by $\beta_c$ activates JAK2 protein-tyrosine kinase (Silvennoinen et al., 1993; Quelle et al., 1994) and subsequently the transcription factor STAT5 is rapidly phosphorylated enabling it to bind to its DNA binding site in the nucleus (Mui et al., 1995; Azam et al., 1995; Gouilleux et al., 1995; Pallard et al., 1995). STAT5 activation therefore represents a relatively immediate response to $\beta_c$-mediated receptor signalling. STAT5 has been described in many haemopoietic cell lines including cells of the myeloid and lymphoid lineages (Mui et al., 1995; Azam et al., 1995; Gouilleux et al., 1995; Pallard et al., 1995). In preliminary experiments we investigated Jurkat T-cells transfected with GM-CSFR, IL-3R or IL-5R receptor α-chain together with wild type $\beta_c$. A cytokine inducible nuclear DNA binding protein was detected that retarded an oligonucleotide probe containing the STAT5 binding consensus sequence (TTC-N$_3$-GAA) in an electrophoretic mobility shift assay. This DNA binding protein was inducible after cytokine treatment in cells transfected with α-chain and $\beta_c$ but not in the absence of $\beta_c$, indicating that $\beta_c$ mediates this ligand-induced process (FIG. 5A). Both the unlabeled probe and the related haemopoitein receptor response element (HRRE) (Morella et al., 1995) competed for binding to the radiolabelled β-casein promoter probe, both of which contain the STAT5 binding consensus sequence. However, a mutant β-casein promoter probe containing mutations in the STAT5 binding consensus and a canonical AP-1 site probe did not compete for binding (FIG. 5B). For this reason we refer to this protein as STAT5-like (STAT5-L) as, although it behaves in a similar fashion to STAT5, its true identity has not been determined.

Figure 6A:
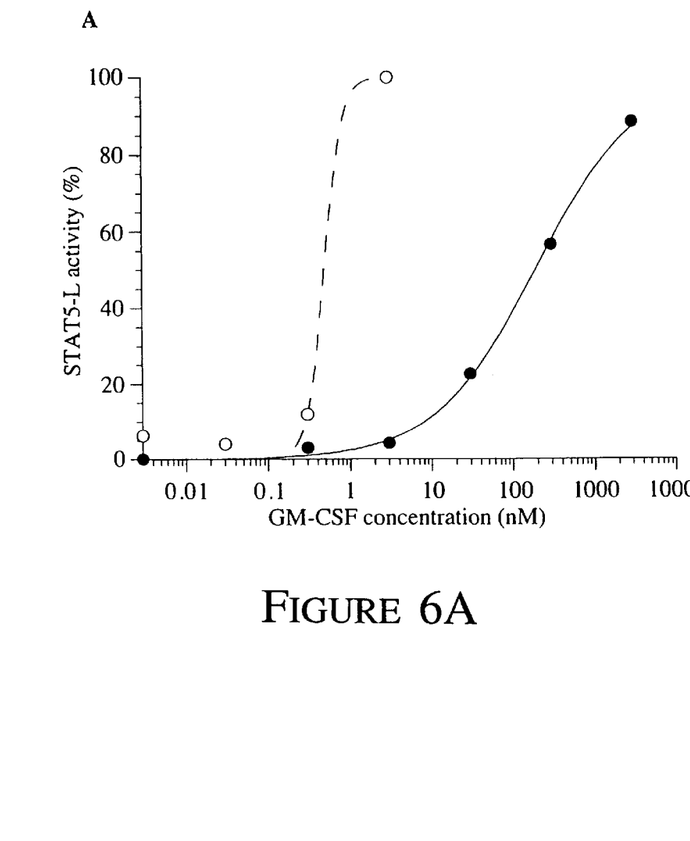
FIG. 6A Is a graphical representation that Y421A $\beta_c$ activates STAT5-L with reduced potency in response to GM-CSF stimulation. A dose-response study of cytokine-induced STAT5-L activity was carried out on Jurkat cells transfected with (x-chains and either wild type $\beta_c$ (o), or Y421A (●). STAT5-L activity was determined by electrophoretic mobility shift assay using a STAT5 specific probe and subsequently quantified by phosphorimager analysis. The results are expressed as a percentage of maximal activity obtained after correction for background and protein concentration.
Figure 6B:
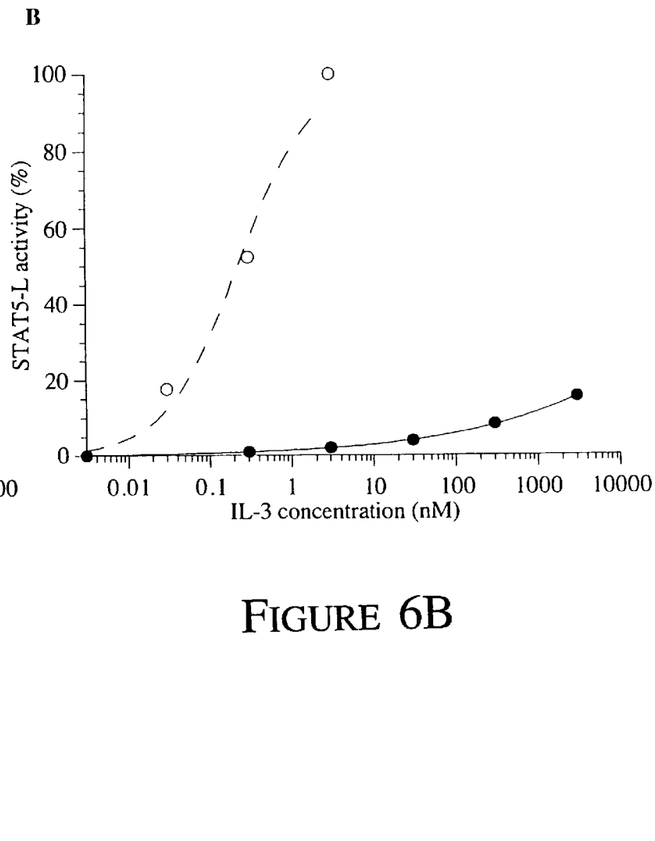
FIG. 6B Is a graphical representation that Y421A $\beta_c$ activates STAT5-L with reduced potency in response to IL-3 stimulation. The experimentation and procedures are as in FIG. 6A.
Figure 7:
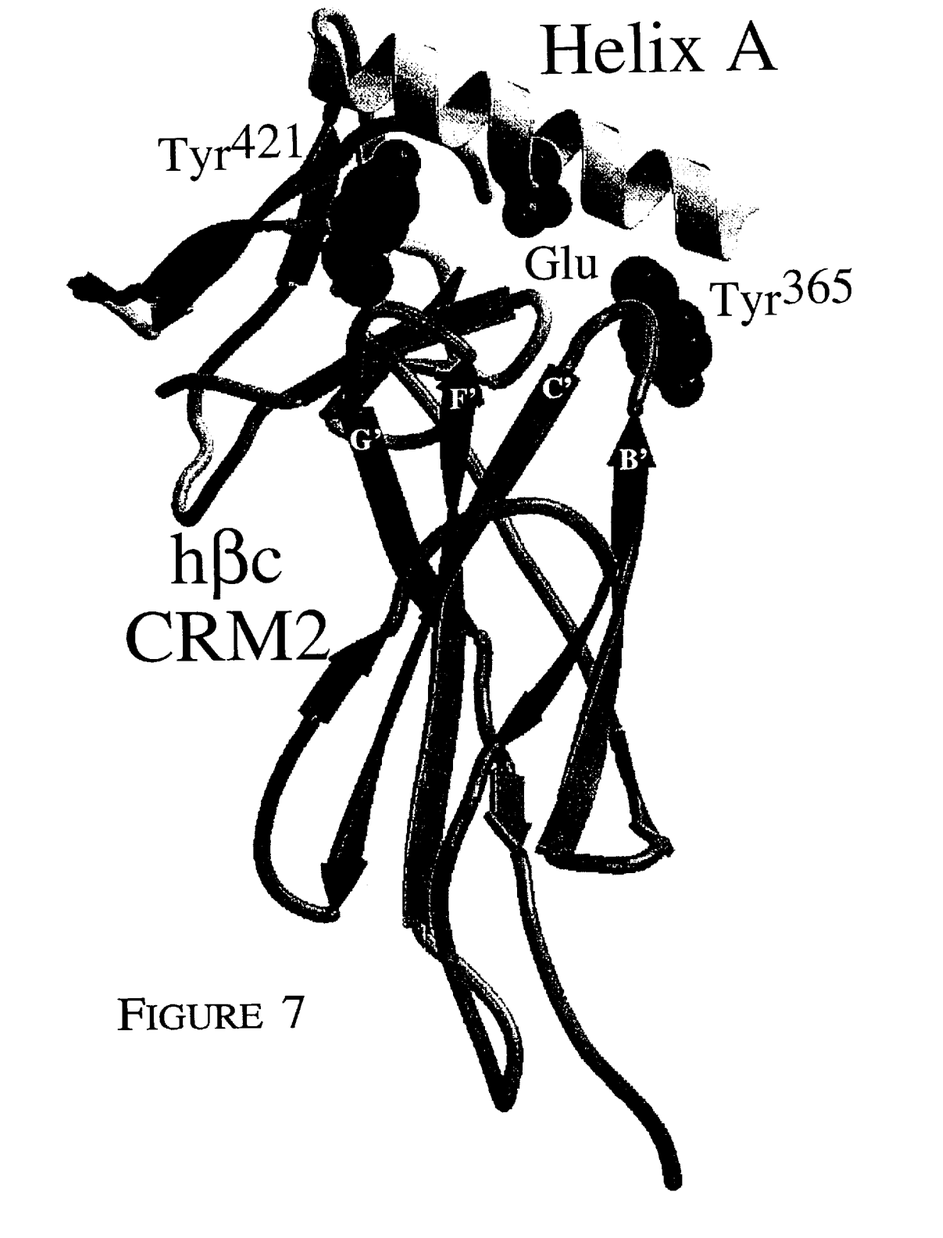
FIG. 7 A model of the special arrangement between the putative B'-C' and F'-G' loops of $\beta_c$ and the first α helix of GM-CSF, IL-3 or IL-5 based on the GH-GHR crystal structure. Only the membrane proximal domains of $\beta_c$ (CRM2) and the first a helix (helix A) of GM-CSF, IL-3 or IL-5 are shown, with Tyr$^{365}$ and Tyr$^{421}$ of $\beta_c$ and the conserved Glu of GM-CSF, IL-3 or IL-5 shown in space-filling representation.

The ability of mutant receptors to activate STAT5-L protein was determined by cotransfecting Jurkat cells with mutant $\beta_c$ and GM-CSFR or IL-3R α-chain cDNAs. Cell surface expression of receptor subunits was confirmed by flow cytometry using chain specific antibodies and the expression of mutant and wild type $\beta_c$ was found to be comparable (data not shown). The transfectants were stimulated with either GM-CSF or IL-3 over a range of concentrations and nuclear extracts prepared. The induction of STAT5-L protein was determined by electrophoretic mobility shift assay (EMSA) using the canonical STAT5 DNA binding site from the β-casein promoter as a probe. STAT5-L was activated in response to either GM-CSF or IL-3 in a dose-dependent fashion in the presence of the appropriate α-chain and wild type $\beta_c$ (FIG. 6A & B). Alanine substitution of Tyr$^{421}$ produced a $\beta_c$ that supported STAT5-L activation in response to GM-CSF with approximately 100–1000 fold reduction in potency (FIG. 6A). This reduction in GM-CSF responsiveness with this mutant $\beta_c$ indicates that Tyr$^{421}$ has a role in GM-CSF induced receptor activation. Significantly, Y421A $\beta_c$ had a greater effect on IL-3-induced STAT5-L activation producing only very low levels of detectable STAT5-L (FIG. 6B) and even at 3 μM IL-3 half maximal activation was not achieved. This suggests that the tyrosine residue is also crucial for the interaction of IL-3 with $\beta_c$.

Example 2

Generation of Antibody Antagonists

Monoclonal antibodies can be generated by immunizing with $\beta_c$ or with a fragment of $\beta_c$ containing the F'-G' loop or with a peptide containing the F'-G' sequence. After specificity controls demonstrate specific binding to the F'-G' loop the antibodies may be selected for blocking GM-CSF, IL-3 and IL-5 high affinity binding and for blocking GM-CSF, IL-3 and IL-5 stimulation of function. Once an appropriate monoclonal antibody has been identified and shown to block GM-CSF/IL-3/IL-5 high affinity binding and function, smaller fragments may be generated; e.g. F(ab)$_2$, Fab and ultimately Fv. By utilising molecular biology techniques a single chain Fv fragment can be constructed (Hv–Lv). This would be an inhibitory peptide.

Example 3

Generation of Peptide Antagonists

Short peptides of similar sequences to the F'-G' loop may be synthesized that block cytokine interaction with the F'-G' loop of $\beta_c$. The reverse is also possible: short peptides of similar sequences to the helix A of GM-CSFIIL-31IL-5 (this is the region in the cytokines predicted to interact with the F'-G' loop) may also block cytokine interaction.

Example 4

Generation of Oligonucleotide Antagonists

A large pool of randomly synthesized oligonucleotides can be passed through an F'-G' peptide immobilized on a solid matrix (Bock et al., 1992,—which reference is incorporated herein). Following washing, the strongly binding oligonucleotides remain and can then be eluted under different conditions (salt, pH etc). The sequence can then be determined by PCR and tested for inhibition of $\beta_c$-mediated function on a real cell system

Example 5

Alignment of Amino Acids of the F-G Loops of $\beta_c$ and gp130

Alignment of the $\beta_c$ and gp130 has been published. gp130 and $\beta_c$ contain domains that are related to the fibronectin type III domain that is a characteristic feature of most cytokine receptors. gp130 has 6 of these domains, $\beta_c$ has four of these domains.

Each domain contains its own F-G loop, thus gp130 has 6 and $\beta_c$ has 4. Only one of these F-G loops is the important one as far as the present invention is concerned. The important domain is characterised by the presence of i) a conserved pattern of Cys residues, ii) several Trp residues iii) a YXXRV/IR motif, and iv) a WSXWS motif (where X is any amino acid). $Tyr^{421}$ is postulated to lie within the F-G loop of the fourth domain loop in $\beta_c$ (F'-G'). The equivalent functionally important tyr in gp130 is postulated to lie within the F-G loop of the second domain.

TABLE 2

Affinity constants and statistical analysis of the binding of GM-CSF, IL-3 and IL-5 to COS cells transfected with the appropriate α chains and wild type or mutant $\beta_c$

| | | | LIGANDS | | | | | | |
|---|---|---|---|---|---|---|---|---|---|
| COS cells expressing: α-chain only[a] | | | GM-CSF $K_d$ = 2–12 nM | | | IL-3 $K_d$ = 20–100 nM | | IL-5 $K_d$ = 1.2–2 nM | |
| | No. of expts | % FACS +ve cells | No. of sites detected | Kd site 1 (pM ± SE) | Kd site 2 (nM ± SE) | No. of sites detected | Kd site 1 (pM ± SE) | No. of expts | Kd site (pM ± SE) |
| +Wild type $\beta_c$ | 10 | 22.8[b] | 2 P < 0.001[c] | 95 ± 17[d] | 5.7 ± 1.7 | 2 P < 0.001 | 141 ± 32[e] | 1 | 644 ± 119[f] |
| +$^{418}$AAAAA$^{422}$ | 4 | 34.2 | 1 | —[g] | 2.9 ± 0.2 | 1 | — | ND[h] | |
| +R418A | 2 | 47.4 | 2 P < 0.001 | 223 ± 74 | 7.0 ± 0.6 | 2 P < 0.001 | 511 ± 156 | ND | |
| +T419A | 2 | 39.1 | 2 P < 0.001 | 105 ± 13 | 13.5 ± 8.0 | 2 P < 0.001 | 151 ± 55 | ND | |
| +G420A | 2 | 39.8 | 2 P < 0.001 | 142 ± 34 | 35.2 ± 9.8 | 2 P < 0.001 | 196 ± 70 | ND | |
| +Y421A | 6 | 34.2 | 1 | — | 2.7 ± 0.3 | 1 | — | 2 | 1858 ± 409 |
| +N422A | 2 | 29.0 | 2 P < 0.001 | 61 ± 64 | 7.8 ± 1.0 | 2 P < 0.001 | 80 ± 53 | ND | |
| +$^{418}$AAAYA$^{422}$ | 3 | 34.5 | 2 P < 0.001 | 295 ± 99 | 10.4 ± 1.3 | 2 P < 0.001 | 113 ± 38 | 2 | 710 ± 132 |

[a]Range of affinities observed for ligand binding to receptor α chain only.
[b]Transfected COS cells positive (+ve) for $\beta_c$ expression measured by fluoresence-activated cell sorter (FACS) using a cocktail of nine anti-$\beta_c$ monoclonal antibodies.
[c]Confidence levels expressed as P values for a one site fit versus a two site fit. Where no confidence level is reported two sites could not be fitted.
[d]Binding data from separate experiments (expts) with GM-CSF were co-analysed and the affinity constants are shown ± the standard error (SE) (Munson and Rodbard, 1980).
[e]Analysis of data was performed as above except that given the extreme low affinity of IL-3 binding to IL-3R α chain, a constant value of 50 nM was used to allow estimation of high affinity sites ($K_d$ site 1).
[f]Analysis of data was performed as above. A single receptor class was detected with IL-5.
[g]—: no high affinity binding sites were detected.
[h]ND: not done.

TABLE 3

Alignment of putative F'-G' loops of members of the cytokine receptor superfamily

| CONSENSUS | V R X R | | W S X W S |
|---|---|---|---|
| | | Common receptor subunits | |
| h$\beta_c$ | V R V R | TSRTGYNGI (SEQ ID No. 1) | W S E W S |
| hLIFR | F R I R | CSTETFWK (SEQ ID No. 2) | W S K W S |
| gp130 (CRM1) | F R I R | CMKEDGKGY (SEQ ID No. 3) | W S P W S |

TABLE 3-continued Alignment of putative F'-G' loops of members of the cytokine receptor superfamily

| CONSENSUS | V R X R | | W S X W S |
|---|---|---|---|
| hIL-2Rβ | V R V K | PLQGE_FT_T (SEQ ID No. 4) | W S P W S |
| hIL-4R/hIL-13R | V R V R V | KTNKLC_F_DDNKL (SEQ ID No. 5) | W S D W S |
| hIL-2Rγ | V R S R | _F_NPLCGSAQH (SEQ ID No. 12) | W S E W S |
| Ligand-specific receptor subunits | | | |
| hIL-3Rα | V Q I R | ERV_YF_F (SEQ ID No. 6) | W S A W S |
| GM-CSFRα | V K I R | AADVR I LN (SEQ ID No. 7) | W S E W S |
| hIL-5Rα | V Q V R | AAVSSMCREAGL (SEQ ID No. 8) | W S E W S |
| Ligand-specific signalling receptors | | | |
| hEPOR | V R A R | MAEPS_F_GG_F_ (SEQ ID No. 9) | W S A W S |
| hTPOR (CRM2) | L R A R | LNGPT_Y_QGP (SEQ ID No. 10) | W S S W S |
| hOBR | V Q V R | CKRLDGLG_Y_ (SEQ ID No. 11) | W S N W S |

Aromatic hydrophobic residues are underlined

REFERENCES

Ackerman et al., (1994) *Chest*, 105;687
Adachi et al., (1995) *Am J Respir Crit Care Med.*, 151, 618
Akir et al (1993) *Adv Immunol* 54, 1–78.
Azam, M. et al. (1995) *EMBO J.*, 14, 1402–1411.
Bagley, C. J., et al. (1995) *J. Leuk. Biol.*, 57, 739–746.
Barry, S. C., et al (1994) *J. Biol. Chem.*, 269, 8488–8492.
Bass, S. H. et al (1991) *Proc. Natl. Acad. Sci. USA*, 88, 4498–4502.
Baumgartner, J. W. et al (1994) *J. Biol. Chem.*, 269, 29094–29101.
Bazan, J. F. (1990) *Proc. Natl. Acad. Sci. USA*, 87, 6934–6938.
Bentley et al, (1996) *Am J respir Crit Care Med* 153, 551
Bock et al., (1992) *Nature* 355, 564–566
Boutin, J. M., et al (1988) *Cell*, 53, 69–77.
Broide et al (1992) *J Clin Invest*, 90, 1414
Clackson, T. and Wells, J. A. (1995) *Science*, 267, 383–386.
Clayberger et al (1991), *J Exp Med* 175, 371
Contreras, M. A. et al (1983) *Methods Ezymol.*, 92, 277–292.
Cosman, D. et al (1990) *Trends Biochem. Sci.*, 17, 265–270.
Cunningham, B. C. et al (1991) *Science*, 254, 821–825.
Davis, S. et al (1993) *Science*, 260, 1805–1810.
De Vos, A. et al (1992) *Science*, 255, 306–312.
Elliott MJ, et al (1989) *Blood* 74, 2349–2359.
Foster et al (1996) *J Exp Med* 183, 195
Fukuda et al., (1994) *J Allergy Clin Immunol.* 94, 584
Gearing, D. P. et al (1991) *EMBO J.*, 10, 2839–2848.
Gearing, D. P. et al (1994) *Proc. Natl. Acad. Sci. USA*, 91, 1119–1123.
Giri, J. G., et al (1994) *EMBO J.*, 13, 2822–2830.
Goodall, G. J. et al (1993) *Growth Factors*, 8, 87–97.
Goodwin, R. G. et al (1990) *Cell*, 60, 941–951.
Gouilleux, F., et al (1995) *EMBO J.*, 14, 2005–2013.
Groopman JE, et al (1987) *New Engl J Med*, 317, 593–598.
Hamid et al., (199 1) *J Clin Invest*, 87, 1541
Hatakeyama, M. et al (1989) *Science*, 244, 551–556.
Hayashida, K. et al (1990) *Proc. Natl. Acad. USA*, 87, 9655–9659.
Hercus, T. R. et al (1994) *Proc. Natl. Acad. Sci. USA*, 91, 5838–5842.
Hibi, M. etal (1990) *Cell*, 63, 1149–1157.
Hilton, D. J. et al (1994) *EMBO J.*, 13, 4765–4775.
Hilton, D. J. et al (1996) *Proc. Natl. Acad. Sci. USA*, 93, 497–501.
Idzerda, R. L. et al (1990) *J. Exp. Med.*, 171, 861–873.
Ip, N.Y. et al (1992) *Cell*, 69, 112–1:132.
Kato M, et al (1992) *Lymphokine Cytokirne Res* 11, 287–292.
Kay A B et al (1991) *J Exp Med* 173, 775–778.
Kimura, Y. et al (1995) *Init. hnwmiol.*, 7, 115–120.
Kitamura, T. et al (1991a) *Cell*, 66, 1165–1174.
Kitamura, T. et al. (1991b) *Proc. Natl. Acad. Sci. USA*, 88, 5082–5086.
Kitamura, T. and Miyajima, A. (1992) *Blood*, 80, 84–90.
Leung, D. W. et al (1987) *Nature*, 330, 537–543.
Liu, J. et al (1992) *J. Biol. Chem.*, 267, 16763–16766.
Lock, P. et al (1994) *Proc. Natl. Acan. Sci. USA*, 91, 252–256.
Lopez A F et al (1989). *Proc Natl Acad Sci USA* 86, 7022–7026.
Lopez et al (1990) *J Cell Physiol*, 145, 69–77
Lopez A F et al (1991) *J Biol Chem* 266, 24741–24747.
Lopez A F et al (1992) *Immunol Today* 13, 495–500.
Lopez, A.F. et al *EMBO J.*, 11, 909–916.
Marini et al., (1992), *Chest* 102, 661
Mauser et al, (1993) *Am Rev Respir Dis*, 148, 1623
Mauser et al (1995) *Am J Repir Crit Care Med* 152, 467
Miyajima, Mol Cell Biol. (1992) *Trends Biocherm Sci* 17, 38–382
Miyazaki, M. et al (1991) *EMBO J.*, 10, 3191–3197.
Morella, K. K. et al (1995) *J. Biol. Chem.*, 270, 8298–8310.
Mui, A. L.-F. et al (1995) *EMBO J.*, 14, 1166–1175.
Munson, P. J. and Rodbard, D. (1980) *Anal. Biochem.*, 107, 220–239.

Nakamura, Y. et al. (1992) *Science*, 257, 1138–1141.
Noguchi, M. et al (1993) Science, 262, 1877–1880.
Pallard, C. et al (1995) *J. Biol. Chem.*, 27, 15942–15945.
Park L S, et al (1989) *Blood*, 74, 56–65.
Patthy, L. (1990) *Cell*, 61, 13–14.
Pennica, D. et al (1995) *J. Biol. Chem.*, 270, 10915–10922.
Quelle, D. E. et al (1992) *Mol. Cell. Biol.*, 12, 4553–4561.
Quelle, F. W. et al (1994) *Mol. Cell Biol*, 14, 4335–4341.
Robinson et al., (1992) *N Engl J Med* 326, 298
Rozakis-Adcock, M. and Kelly, P. A. (1992) *J. Biol. Chem.*, 267, 7428–7433.
Russell, S. M. et al (1993) *Science*, 262, 1880–1883.
Shanafelt, A. B. and Kastelein, R. A. (1992) *J. Biol. Chem.*, 267, 25466–25472.
Silvennoinen, O. et al (1993) *Proc. Natl. Acad. Sci. USA*, 90, 8429–8433.
Somers, W. et al (1994) *Nature*, 372, 478–481.
Sur et al., (1995) *J Allergy Clin Immunol*, 96, 661
Sur et al., (1996) *J Allergy Clin Immunol*, 97, 1272
Taga, T. et al (1992) *Proc. Natl. Acad. Sci. USA*, 89, 10998–11001.
Takaki, S. et al (1993) *J. Exp. Med.*, 177, 1523–1529.
Takeshita, T. et al (1992) *Science*, 257, 379–382.
Tartaglia et al., (1995) *Cell* 83, 1263–1271
Tavernier, J. et al (1991) *Cell*, 66, 1175–1184.
Vigon, I. et al (1992) *Proc. Natl. Acad. Sci. USa*, 89, 5640–5644.
Williamson D J et al (1988) *Clin Exp Immunol* 72, 67–73.
Woodcock, J. M. et al (1994) *EMBO J.*, 13, 5176–5185.
Xing et al., (1996) *J Clin Invest* 97, 1102–1110
Yamasaki, K. et al (1988) *Science*, 241, 825–828.
Yawata, H. et al (1993) *EMBO J.*, 12, 1705–1712.
Yoshimura, A. et al (1992) *J. Biol. Chem.*, 267, 11619–11625.
Young D C, Griffin J D. (1986) *Blood* 68, 1178–1181.
Zangrilli et al., (1995) *Am J Respir Crit Care Med* 151, 1346
Zurawski, S. M. et al (1993) *EMBO J.*, 12, 2663–2670.

What is claim is:

1. An antibody that binds to the common $\beta_c$ chain of the receptor for GM-CSF, IL-3 and IL-5, said common $\beta_c$ chain having the amino acid sequence set forth in SEQ ID NO: 1, wherein said antibody antagonizes the effects of GM-CSF, IL-3 or IL-5 by inhibiting the binding of the cytokine to the common $\beta_c$ chain.

2. An antibody according to claim 1 which binds to $Tyr^{421}$ of SEQ. ID NO:1 of the common $\beta_c$ chain of the receptor for GM-CSF, IL-3 and IL-5.

3. An antibody according to claim 2 which inhibits bindng between $Tyr^{421}$ of SEQ ID NO:1 of the common $\beta_c$ chain and any one of GM-CSF, IL-3 and IL-5.

4. An antibody according to claim 2 which inhibits binding between $Tyr^{421}$ of SEQ ID NO:1 of the common $\beta_c$ chain and all of GM-CSF, IL-3 and IL-5.

5. An antibody according to claim 2 wherein the cytokine receptor is selected from the group consisting of GM-CSFR, IL-5R and IL-3R.

* * * * *